(12) United States Patent
Hattori et al.

(10) Patent No.: US 12,105,276 B2
(45) Date of Patent: Oct. 1, 2024

(54) CONNECTOR DEVICE FOR ENDOSCOPE

(71) Applicant: FUJIFILM Corporation, Tokyo (JP)

(72) Inventors: Shintaro Hattori, Kanagawa (JP); Nobuyuki Torisawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 535 days.

(21) Appl. No.: 17/407,116

(22) Filed: Aug. 19, 2021

(65) Prior Publication Data
US 2021/0382291 A1 Dec. 9, 2021

Related U.S. Application Data

(63) Continuation of application No. PCT/JP2020/011161, filed on Mar. 13, 2020.

(30) Foreign Application Priority Data

Mar. 19, 2019 (JP) .................. 2019-050668

(51) Int. Cl.
*H01R 13/52* (2006.01)
*G02B 23/24* (2006.01)
(Continued)

(52) U.S. Cl.
CPC ..... *G02B 23/2469* (2013.01); *G02B 23/2476* (2013.01); *H01R 13/5202* (2013.01); *H01R 13/629* (2013.01); *H01R 13/7172* (2013.01)

(58) Field of Classification Search
CPC ............ G02B 23/2469; G02B 23/2476; H01R 13/5202; H01R 13/629; H01R 13/7172
See application file for complete search history.

(56) References Cited

U.S. PATENT DOCUMENTS 7,850,601 B2 12/2010 Uchimura et al.
8,345,092 B2 * 1/2013 Takasaki ................ H04N 23/54
257/680
(Continued)

FOREIGN PATENT DOCUMENTS

CN 1542536 11/2004
CN 1942133 4/2007
(Continued)

OTHER PUBLICATIONS

"International Search Report (Form PCT/ISA/210) of PCT/JP2020/011161," mailed on Jun. 16, 2020, with English translation thereof, pp. 1-5.
(Continued)

*Primary Examiner* — Thanh Tam T Le
(74) *Attorney, Agent, or Firm* — JCIPRNET (57) ABSTRACT

A connector device for an endoscope that can stably operate an endoscope is provided. A connector device (10) includes a hollow exterior case (20), a shield case (22) accommodated in the exterior case (20), and a power reception unit (24) to which power is supplied from a power feed unit (216) of a processor device (200) in a contactless manner. The exterior case (20) has a side wall part (32D) that faces the power feed unit (216). The shield case (22) has an inner case wall part (23) that is disposed to face and be spaced apart from the side wall part (32D). The power reception unit (24) is disposed on the inner case wall part (23).

13 Claims, 9 Drawing Sheets

(51) Int. Cl.
 *H01R 13/629* (2006.01)
 *H01R 13/717* (2006.01)

(56) References Cited

U.S. PATENT DOCUMENTS

| | | | |
|---|---|---|---|
| 8,681,207 B2 * | 3/2014 | Tsujimura | G02B 23/2484 |
| | | | 348/65 |
| 8,696,657 B2 | 4/2014 | Matsunaga et al. | |
| 8,896,680 B2 | 11/2014 | Okawa et al. | |
| 9,065,107 B2 | 6/2015 | Bennett et al. | |
| 9,118,057 B2 | 8/2015 | Bennett et al. | |
| 9,486,268 B2 | 11/2016 | Bennett et al. | |
| 10,058,239 B2 | 8/2018 | Hara et al. | |
| 10,070,778 B2 | 9/2018 | Hara et al. | |
| 10,231,603 B2 * | 3/2019 | Ogura | A61B 1/00016 |
| 10,327,623 B2 | 6/2019 | Hara et al. | |
| 10,398,297 B2 | 9/2019 | Ide et al. | |
| 10,463,231 B2 | 11/2019 | Hara | |
| 10,492,664 B2 | 12/2019 | Narita | |
| 10,608,371 B1 * | 3/2020 | Ramotowski | H01R 43/005 |
| 10,993,605 B2 * | 5/2021 | Levy | A61B 1/00126 |
| 11,234,581 B2 * | 2/2022 | Salman | B65G 69/2882 |
| 2012/0088970 A1 | 4/2012 | Kato et al. | |
| 2014/0184771 A1 | 7/2014 | Mazzetti et al. | |
| 2016/0089000 A1 | 3/2016 | Hara | |
| 2016/0367115 A1 | 12/2016 | Ogura et al. | |

FOREIGN PATENT DOCUMENTS

| | | |
|---|---|---|
| CN | 102209504 | 10/2011 |
| CN | 104335386 | 2/2015 |
| CN | 104939799 | 9/2015 |
| CN | 106175649 | 12/2016 |
| CN | 106175653 | 12/2016 |
| CN | 106235994 | 12/2016 |
| CN | 106714647 | 5/2017 |
| CN | 107049205 | 8/2017 |
| CN | 208044188 | 11/2018 |
| EP | 3245933 | 11/2017 |
| JP | H07191268 | 7/1995 |
| JP | H0966024 | 3/1997 |
| JP | H11202218 | 7/1999 |
| JP | 2001149311 | 6/2001 |
| JP | 2002345731 | 12/2002 |
| JP | 2006320381 | 11/2006 |
| JP | 2016064050 | 4/2016 |
| JP | 2016067534 | 5/2016 |
| JP | 2016067535 | 5/2016 |
| JP | 2017006217 | 1/2017 |
| WO | 2010122770 | 10/2010 |
| WO | 2013042647 | 3/2013 |

OTHER PUBLICATIONS

"Written Opinion of the International Searching Authority (Form PCT/ISA/237)" of PCT/JP2020/011161, mailed on Jun. 16, 2020, with English translation thereof, pp. 1-8.

"Search Report of Europe Counterpart Application", issued on Apr. 8, 2022, p. 1-p. 8.

Wang Yunlong, "Research on quality control qualitative testing technology of medical endoscope's optical performance" with English Abstract, Thesis of Master Degree, SMU, Apr. 2015, pp. 1-77.

Takuya Chishiro et al., "Multiarticular Manipulator and Its Multi Degree of Freedom Motion By Distributed Thin Piston-Cylinder Actuators," Transducers 2013, Jun. 2013, pp. 1579-1582.

"Office Action of Japan Counterpart Application" with English translation thereof, issued on Nov. 1, 2022, p. 1-p. 16.

* cited by examiner

CONNECTOR DEVICE FOR ENDOSCOPE

CROSS-REFERENCE TO RELATED APPLICATIONS

The present application is a Continuation of PCT International Application No. PCT/JP2020/011161 filed on Mar. 13, 2020 claiming priority under 35 U.S.C. § 119(a) to Japanese Patent Application No. 2019-050668 filed on Mar. 19, 2019. Each of the above applications is hereby expressly incorporated by reference, in its entirety, into the present application.

BACKGROUND OF THE INVENTION

1. Field of the Invention

The present invention relates to a connector device for an endoscope, and particularly relates to a connector device for an endoscope connected to a processor device for an endoscope.

2. Description of the Related Art

A connector device for an endoscope (first connector) comprising a power reception coil is disclosed in JP2016-67534A. In a case where the connector device is connected to a processor device for an endoscope, a contactless power supply unit is composed of the power reception coil and a power feeding coil on a processor device for an endoscope side, and power necessary for an endoscope is supplied by the power supply unit from the processor device for an endoscope to the endoscope.

In addition, the connector device of JP2016-67534A comprises an exterior case having a first connector case, a second connector case, and a third connector case in order from a side connected to the processor device for an endoscope, and the power reception coil is disposed at a position close to a surface connected to the processor device for an endoscope, inside the first connector case.

SUMMARY OF THE INVENTION

In the connector device comprising the power reception coil as in JP2016-67534A, in order to guarantee a stable operation of the endoscope, it is necessary for the positions of the power feeding coil of the processor device for an endoscope and the power reception coil of the connector device are accurately aligned.

However, for example, in a case where the power reception coil is disposed in the exterior case of the connector device, there are the following problems. That is, it is necessary for the endoscope to be sterilized each time the endoscope is used. In this case, sterilization is performed using an autoclave in some cases, but the connector device at the time of sterilization is exposed to high-temperature and high-pressure (for example, 121° C. and 2 atm) saturated steam for approximately 20 minutes. In a case where such sterilization is repeatedly performed, the shape of the exterior case of the connector device gradually deforms due to a heat cycle of the steam sterilization. Thus, the position of the power reception coil deviates from the initial position, and as a result, there are problems that the feeding efficiency decreases and the operation of the endoscope becomes unstable.

The present invention is devised in view of such circumstances, and an object thereof is to provide a connector device for an endoscope that can stably operate an endoscope.

According to an aspect of the present invention, in order to achieve the object of the present invention, there is provided a connector device for an endoscope that is attachably and detachably connected to a processor device. The connector device for an endoscope comprises a hollow exterior case, an inner case that is accommodated inside the exterior case, a holding body that is used for disposing the inner case inside the exterior case, and a power reception unit to which power is supplied from a power feed unit of the processor device in a contactless manner. The exterior case has a side wall part that faces the power feed unit of the processor device. The inner case has an inner case wall part that is disposed to face and be spaced apart from the side wall part. The power reception unit is disposed on the inner case wall part.

In the aspect of the present invention, it is preferable that the power reception unit has a flat plate-shaped core and a coil that is spirally wound around the core, and the core is composed of a sintered ferrite core.

In the aspect of the present invention, it is preferable that the power reception unit is adhered to the inner case wall part by a thermosetting adhesive material.

In the aspect of the present invention, it is preferable that the holding body is a shaft-shaped member of which one end is fixed to the inner case wall part, a first lead-out hole, into which the shaft-shaped member is inserted and which leads the other end of the shaft-shaped member to an outside of the exterior case, is provided in the side wall part, and a first sealing member is arranged between an inner wall surface of the first lead-out hole and an outer wall surface of the shaft-shaped member.

In the aspect of the present invention, it is preferable that the processor device has a positioning hole, into which the other end of the shaft-shaped member is inserted, in a surface facing the side wall part, and the other end of the shaft-shaped member is inserted into the positioning hole, and the power reception unit is in a state of being positioned at a position facing the power feed unit.

In the aspect of the present invention, it is preferable that the first sealing member is an O-ring fitted to the outer wall surface of the shaft-shaped member.

In the aspect of the present invention, it is preferable that the exterior case is made of a resin, and the inner case is made of a metal.

In the aspect of the present invention, it is preferable that the inner case is a shield case for shielding an electronic component.

In the aspect of the present invention, it is preferable that the exterior case has a cylindrical body, the inner case is formed in a rectangular parallelepiped shape, and the inner case is accommodated in the exterior case in a posture in which a long side of the inner case is aligned with an axis of the cylindrical body.

In the aspect of the present invention, it is preferable that the exterior case has an opening portion to which a universal cable extending from an endoscope is connected, and a second sealing member is arranged between an inner wall surface of the opening portion and an outer wall surface of the universal cable.

In the aspect of the present invention, it is preferable that the second sealing member is an O-ring fitted to the outer wall surface of the universal cable.

In the aspect of the present invention, it is preferable that the opening portion of the exterior case is formed in a size that allows the endoscope, the universal cable, and a switch disposed member provided at the universal cable to be inserted therein.

In the aspect of the present invention, it is preferable that the connector device for an endoscope further comprises a light guide rod of which one end is disposed inside the exterior case, a second lead-out hole, into which the light guide rod is inserted and which leads the other end of the light guide rod to an outside of the exterior case, is provided in the side wall part, and a third sealing member is arranged between an inner wall surface of the second lead-out hole and an outer wall surface of the light guide rod.

In the aspect of the present invention, it is preferable that the third sealing member is an O-ring fitted to the outer wall surface of the light guide rod.

With the present invention, the endoscope can be stably operated.

DESCRIPTION OF THE PREFERRED EMBODIMENTS

Hereinafter, a connector device for an endoscope according to an embodiment of the present invention will be described with reference to the accompanying drawings.

Figure 1:
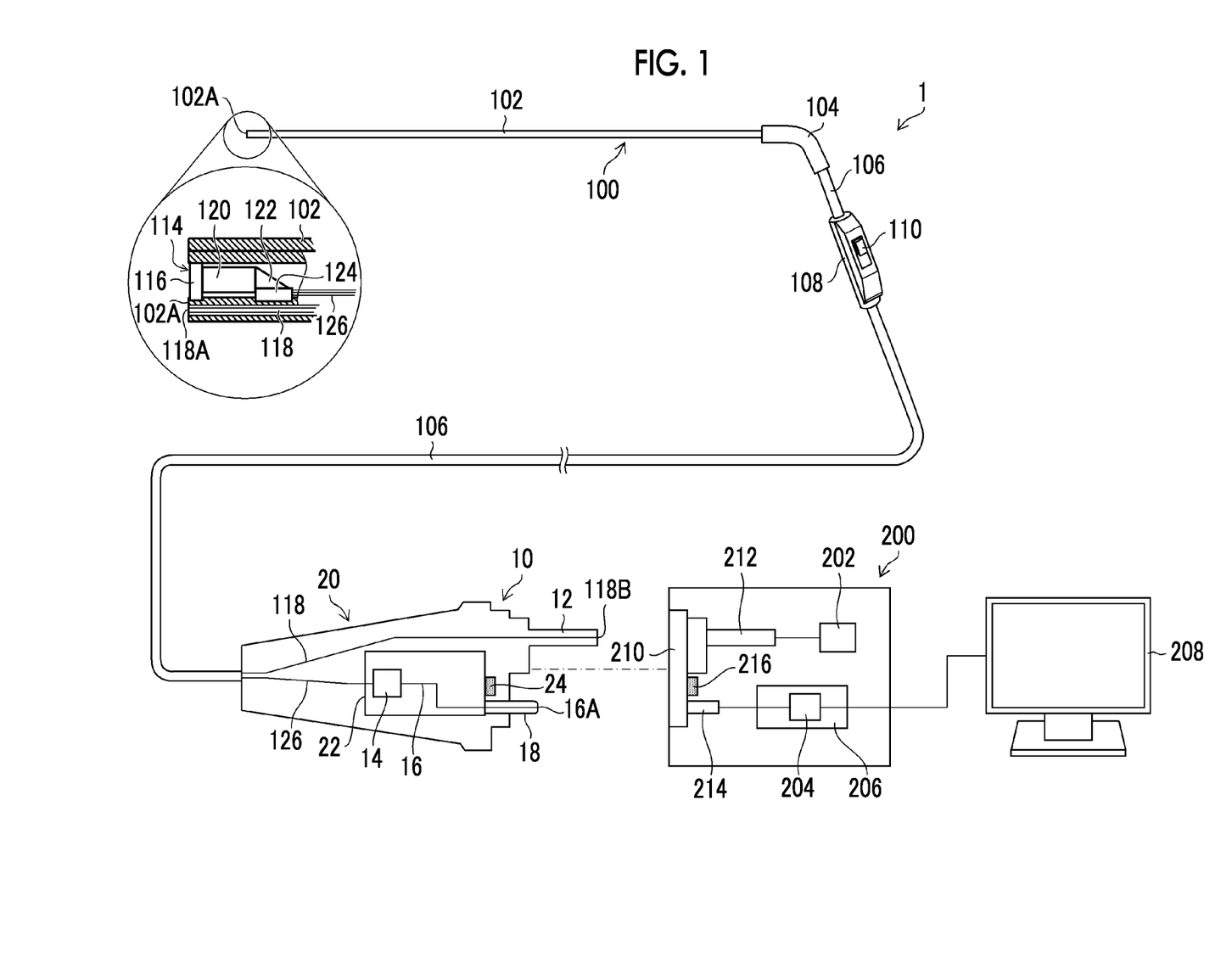
FIG. 1 is a schematic configuration view of an endoscope system.

FIG. 1 is a schematic configuration view of an endoscope system 1. The endoscope system 1 comprises an endoscope 100 and a processor device for an endoscope 200.

The endoscope 100 is a rigid endoscope, such as a laparoscope, and comprises an elongated rigid insertion part 102 that is inserted into a body cavity, an L-shaped grip portion 104 continuously connected to a proximal end part of the insertion part 102, a flexible universal cable 106 of which a proximal end part is connected to the insertion part 102 via the grip portion 104, and a switch disposed member 108 provided in a middle portion of the universal cable 106.

A connector device 10 according to the embodiment is provided at a tip part of the universal cable 106, and the endoscope 100 is attachably and detachably connected to a processor side connector 210 of the processor device for an endoscope 200 via the connector device 10. FIG. 1 illustrates the connector device 10 in an exaggerated manner as compared with the endoscope 100.

The processor device for an endoscope 200 comprises an image processing unit 206, which includes a light source unit 202, and an image signal reception unit 204. In addition, a monitor 208 that displays an image which is image-processed by the image processing unit 206 is connected to the processor device for an endoscope 200.

The endoscope system 1 of the present example has a configuration that transmits power, optical signals, and the like in a contactless manner between the endoscope 100 and the processor device for an endoscope 200 via a connector part composed of the connector device 10 and the processor side connector 210. In addition, as an operation switch 110 disposed on the switch disposed member 108 described above, for example, an image changeover switch that switches an image to be displayed on the monitor 208 between a normal captured image and a special light image (for example, a white light (WL) image, a blue laser imaging (BLI) image, a linked color imaging (LCI) image, or a hypoxia imaging image) can be applied. In addition, without being limited to the image changeover switch, an image immobilizing switch, an imaging switch, a zoom switch comprising a telephoto and wide-angle button, a insertion part tip part washing switch, a light amount adjusting switch, a sensitivity adjusting switch, or the like can also be applied.

Figure 2:
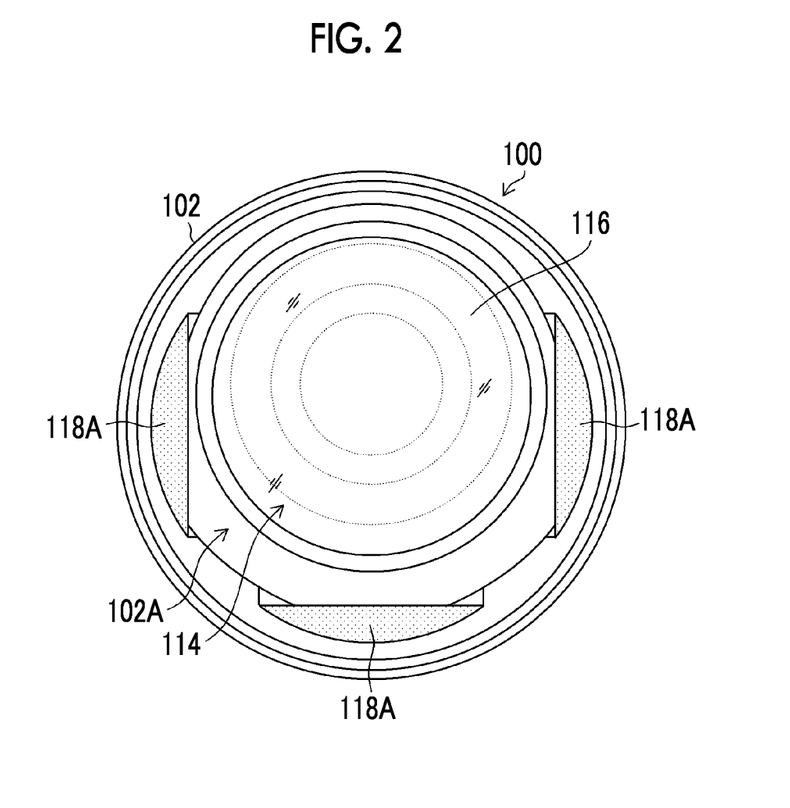
FIG. 2 is a front view of a tip part of an insertion part.

FIG. 2 is a front view of a tip part of the insertion part 102. In addition, FIG. 1 illustrates an enlarged cross section of main parts at the tip part of the insertion part 102.

As illustrated in FIGS. 1 and 2, an observation part 114 is provided on a distal end surface 102A of the insertion part 102. The observation part 114 comprises an observation window 116, three light emission ends 118A that are tip parts of a light guide 118, which is disposed around the observation window 116, an image pick-up lens group 120 and a prism 122 that are disposed behind the observation window 116, and a solid-state imaging element 124. As the solid-state imaging element 124, a charge coupled device (CCD) image sensor or a complementary metal oxide semiconductor (CMOS) image sensor can be applied.

A proximal end part of the light guide 118 is inserted into the insertion part 102, the grip portion 104, and the universal cable 106, and is disposed to be inserted in a cylindrical light guide rod 12 of the connector device 10. By connecting the light guide rod 12 to a connection hole 212 of the processor side connector 210, a light incident end 118B of the light guide 118 is connected to the light source unit 202 of the processor device for an endoscope 200. Accordingly, illumination light from the light source unit 202 is transmitted via the light guide 118, and is radiated to the front of the insertion part 102 from the three light emission ends 118A of the light guide 118.

On the other hand, subject light picked up from the observation window 116 is formed as an image on an imaging surface of the solid-state imaging element 124 via the image pick-up lens group 120 and the prism 122, and is converted to an image pick-up signal by the solid-state imaging element 124. A tip part of a signal line 126 is connected to the solid-state imaging element 124 via a base substrate (not illustrated). A proximal end part of the signal line 126 is inserted into the insertion part 102, the grip portion 104, and the universal cable 106, and is connected to an image signal transmission unit 14 accommodated in an exterior case 20 of the connector device 10. The image pick-up signal is converted to an optical signal by the image signal transmission unit 14, and the optical signal is transmitted to a fiber cable 16 accommodated in the exterior case 20.

A light emission end 16A of the fiber cable 16 is disposed to be inserted in a cylindrical pin 18 of the connector device 10. By connecting the pin 18 to a connection hole 214 of the processor side connector 210, the optical signal is optically transmitted to the image signal reception unit 204 of the processor device for an endoscope 200 in a contactless manner. The optical signal optically transmitted to the image signal reception unit 204 is image-processed by the image processing unit 206 and is displayed on the monitor 208 as a subject image.

The pin 18 is an example of a shaft-shaped member, which is a component of the present invention. A proximal end part of the pin 18 is fixed to a metal shield case 22 accommodated inside the exterior case 20, and the shield case 22 is positioned at the processor side connector 210 by connecting the pin 18 to the connection hole 214. In addition, an electronic component such as a substrate configuring the image signal transmission unit 14 is mounted inside the shield case 22.

The connector device 10 is provided with a power reception unit 24 that receives power in a contactless manner, and the processor side connector 210 is provided with a power feed unit 216 that feeds power in a contactless manner. In the endoscope system 1 of the present example, a contactless power supply unit is composed of the power feed unit 216 and the power reception unit 24, and power necessary for driving an electronic component on an endoscope 100 side is supplied by the power supply unit from the processor device for an endoscope 200 to the connector device 10. As will be described later, the power reception unit 24 is not fixed to the exterior case 20, and is fixed to the shield case 22 like the pin 18.

In a case where the connector device 10 is connected to the processor side connector 210 via the light guide rod 12 and the pin 18, the power feed unit 216 and the power reception unit 24 are disposed near to face each other at a distance allowing electromagnetic coupling, and are in a state where power feeding from the power feed unit 216 to the power reception unit 24 is possible in a contactless manner. The power feed unit 216 is connected to an external commercial power source, and in a case where power is supplied from the commercial power source to the power feed unit 216, power is fed in a contactless manner from the power feed unit 216 to the power reception unit 24.

A primary coil (also referred to as a power feeding coil) connected to the commercial power source can be given as an example of the power feed unit 216, and a secondary coil (also referred to as a power reception coil) electromagnetically coupled to the primary coil can be given as an example of the power reception unit 24.

A structure in which a coil is spirally wound around a surface of a flat plate-shaped core can be given as an example of the structures of the primary coil and the secondary coil. In this case, a core of the secondary coil configuring the power reception unit 24 is preferably, for example, a highly heat-resistant sintered ferrite core. Accordingly, the highly heat-resistant power reception unit 24 that can withstand the heat of an autoclave can be configured. In addition, the power reception unit 24 is fixed to the shield case 22 as will be described later. However, in this case, it is preferable to adhere the power reception unit 24 to the shield case 22, for example, using a thermosetting adhesive material such as a highly heat-resistant thermosetting epoxy sheet. Accordingly, the highly heat-resistant power reception unit 24 can be configured.

The power supply unit in which the power feed unit 216 is configured by the primary coil and the power reception unit 24 is configured by the secondary coil is given as an example of the contactless power supply unit in the embodiment, but without being limited thereto, may be a power supply unit that can feed and receive power in a contactless manner. Since an endoscope that feeds power using the primary coil and the secondary coil is known in JP2016-67534A, detailed description thereof will be omitted herein.

Figure 3:
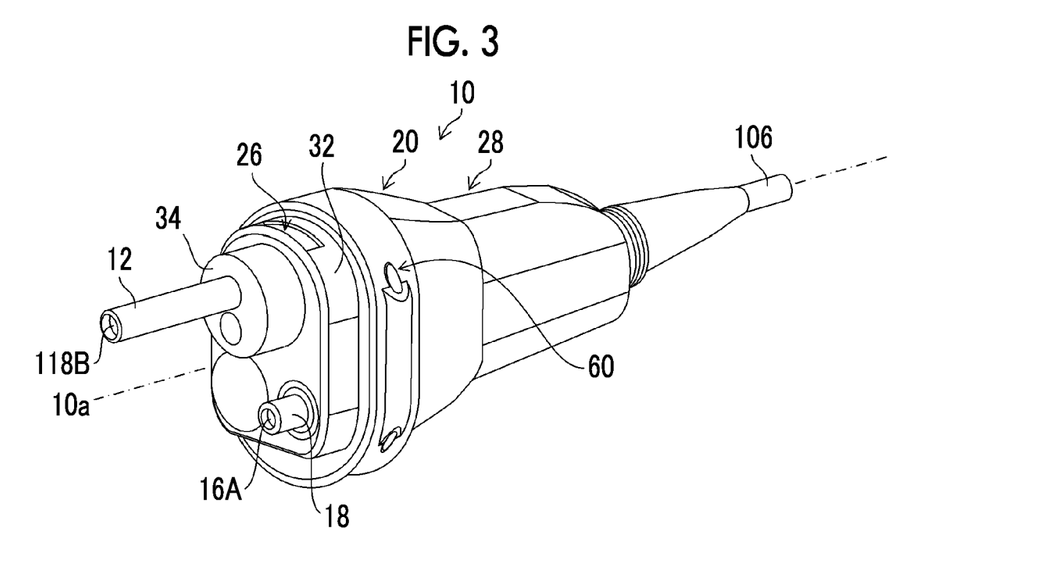
FIG. 3 is an external perspective view of a connector device.

Next, a structure of the connector device 10 will be described. FIG. 3 is an overall perspective view illustrating the appearance of the connector device 10.

As illustrated in FIG. 3, the exterior case 20 of the connector device 10 has a longitudinal axis 10a parallel to an axial direction of the cylindrical light guide rod 12 and the pin 18. In the following description, a position and a direction of a space where the connector device 10 is disposed will be described using the following terms. An X(+) direction and an X(−) direction along the longitudinal axis 10a are the "front" and the "rear" respectively, a Y(+) direction and a Y(−) direction orthogonal to the X-direction are the "left" and the "right" respectively, and a Z(+) direction and a Z(−) direction orthogonal to the XY-directions are the "up" and the "down" respectively.

The connector device 10 has the highly heat-resistant and chemical-resistant resin exterior case 20, the metal light guide rod 12, the metal pin 18, and the metal shield case 22 (see FIG. 1).

Figure 4:
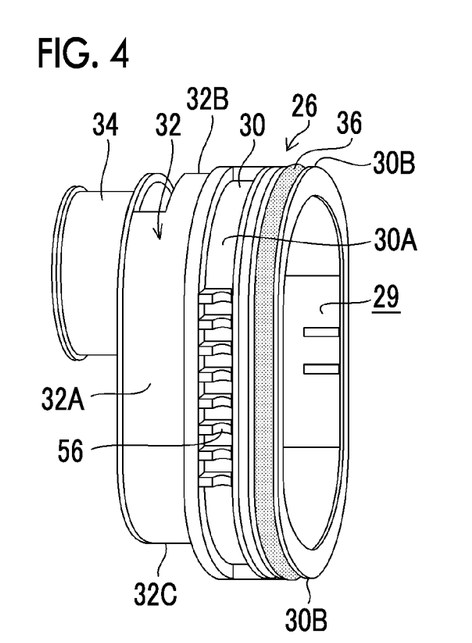
FIG. 4 is a perspective view of a plug configuring an exterior case.
Figure 5:
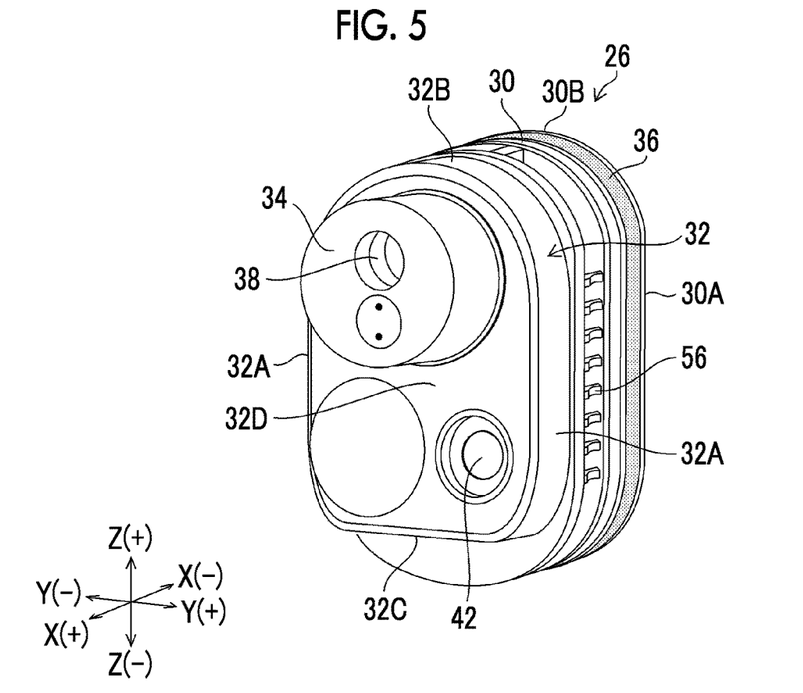
FIG. 5 is a perspective view of the plug viewed from the front toward the rear.
Figure 6:
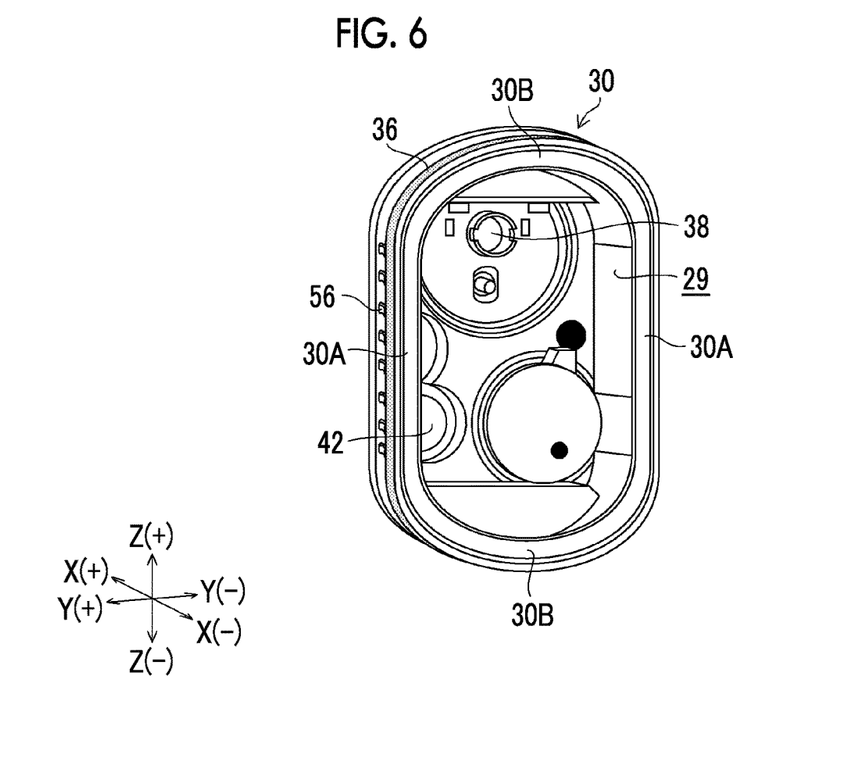
FIG. 6 is a perspective view of the plug viewed from the rear toward the front.

FIG. 4 is a perspective view of a plug 26 configuring the exterior case 20. FIG. 5 is a perspective view of the plug 26 viewed from the front toward the rear. FIG. 6 is a perspective view of the plug 26 viewed from the rear toward the front.

Figure 7:
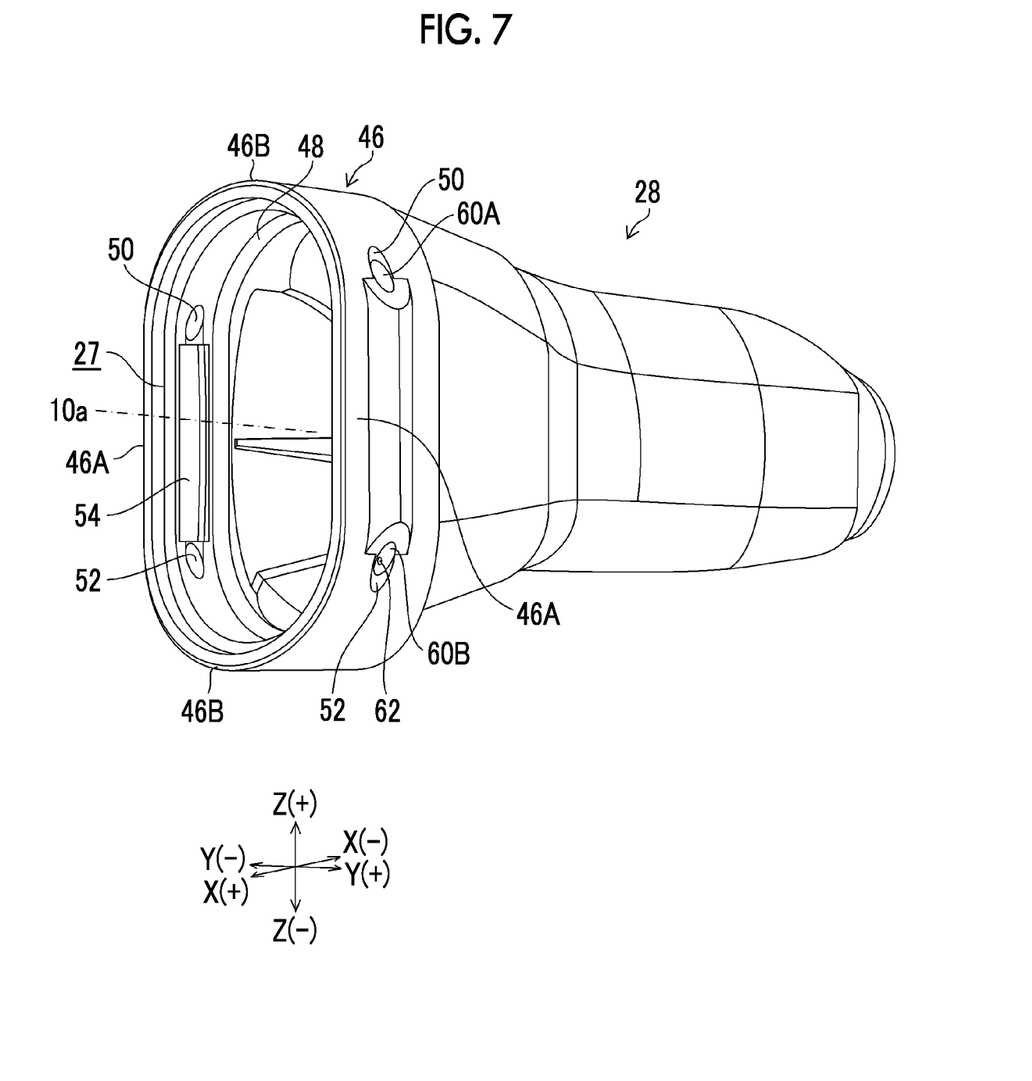
FIG. 7 is a perspective view of a connector exterior case configuring the exterior case viewed from the front toward the rear.
Figure 8:
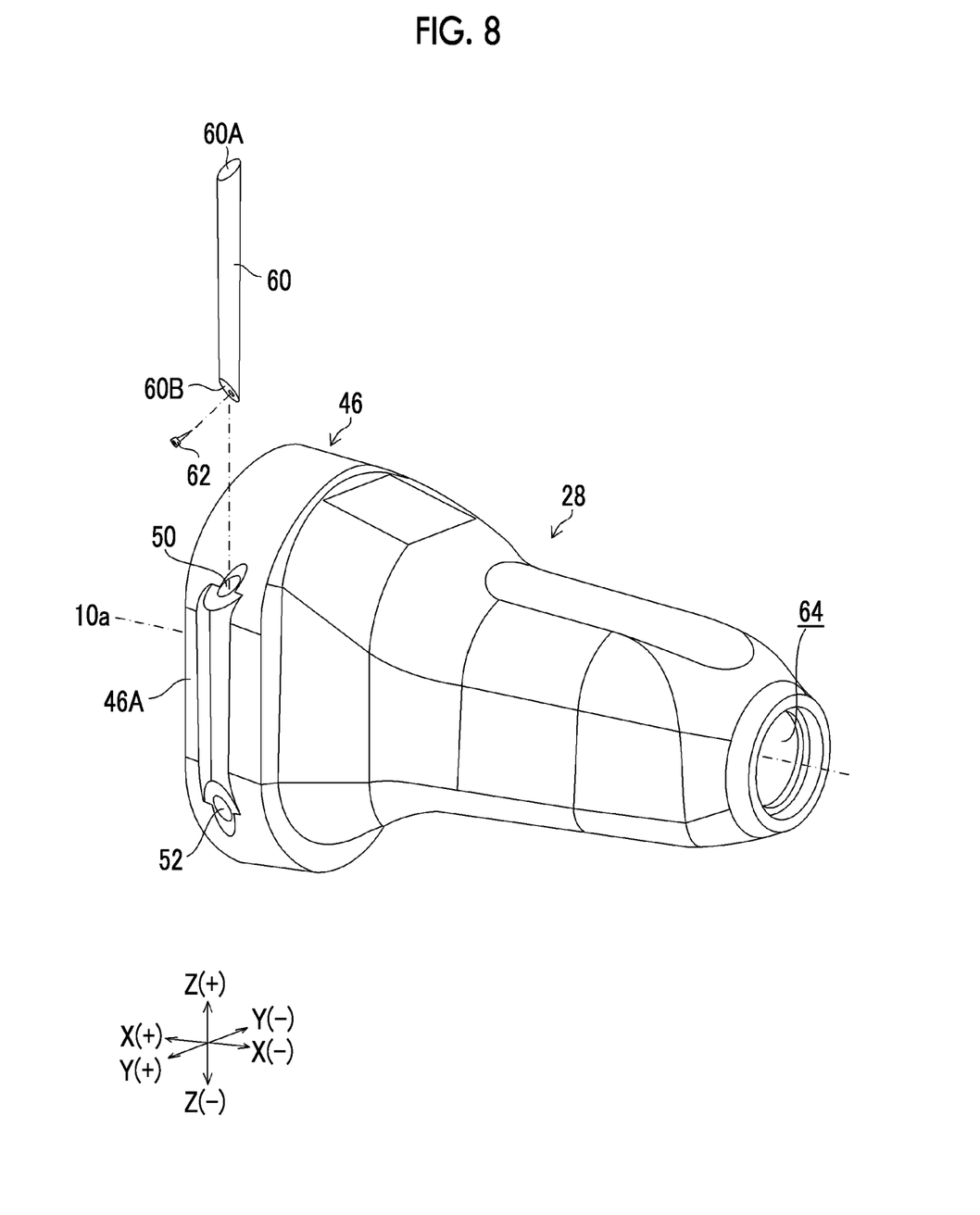
FIG. 8 is a perspective view of the connector exterior case viewed from the rear toward the front.

In addition, FIG. 7 is a perspective view of a connector exterior case 28 configuring the exterior case 20 viewed from the front toward the rear. FIG. 8 is a perspective view of the connector exterior case 28 viewed from the rear toward the front.

Referring back to FIG. 3, the exterior case 20 is formed in a hollow shape by connecting the plug 26 illustrated in FIGS. 4 to 6 to the connector exterior case 28 illustrated in FIGS. 7 and 8.

As illustrated in FIGS. 4 to 6, the plug 26 comprises an elliptical ring portion 30 that has an opening 29 in a rear end, a mount portion 32 that protrudes from the elliptical ring portion 30 toward the front, and a cylindrical portion 34 that protrudes from the mount portion 32 toward the front.

As illustrated in FIG. 6, the elliptical ring portion 30 is configured to have a shape in plan view that is a race track shape (oval shape), in which a pair of parallel linear portions 30A and 30A, which face each other in a right-and-left direction, and a pair of curved portions 30B and 30B, which face each other in an up-and-down direction, are connected to each other. In addition, an O-ring 36, which is a sealing member, is fitted to an outer peripheral surface of the elliptical ring portion 30. The O-ring 36 is also one of a plurality of sealing members that seal the inside of the exterior case 20, as will be described later.

As illustrated in FIG. 5, the mount portion 32 is configured to have a shape in plan view that is a substantially semi-elliptical shape, in which a pair of parallel linear portions 32A and 32A, which face each other in the right-and-left direction, and the curved portion 32B and a linear portion 32C, which face each other in the up-and-down direction, are connected to each other.

The cylindrical portion 34 is provided on an upper part of a side wall part 32D of the mount portion 32 and comprises, in a center part thereof, a lead-out hole 38 that leads the light guide rod 12 (see FIG. 3) to the outside. The lead-out hole 38 is an example of a second lead-out hole, which is a component of the present invention. In addition, the side wall part 32D is an example of a side wall part, which is a component of the present invention. In a case where the connector device 10 is connected to the processor device for an endoscope 200, the side wall part 32D is disposed to face the power feed unit 216 (see FIG. 1) of the processor device for an endoscope 200.

Figure 9:
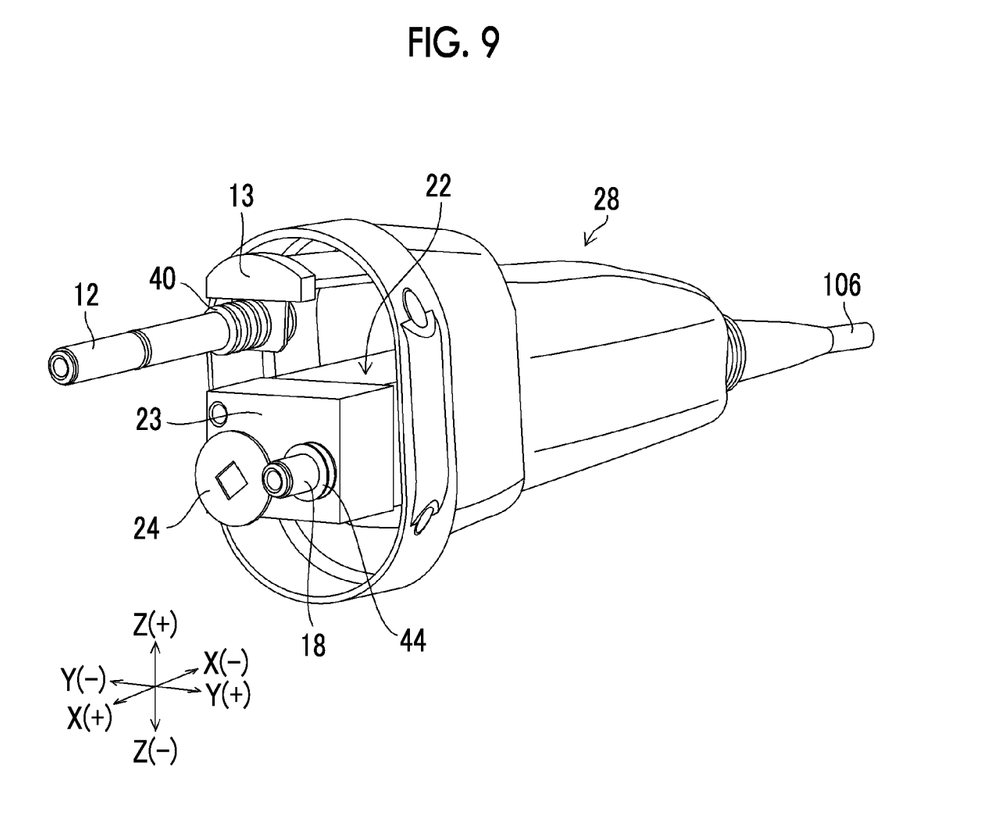
FIG. 9 is a perspective view of the connector exterior case including a light guide rod viewed from the front toward the rear.

FIG. 9 is a perspective view of the connector exterior case 28 viewed from the front toward the rear, and illustrates the light guide rod 12 and the shield case 22. As illustrated in FIG. 9, the light guide rod 12 has a proximal end part disposed inside the exterior case 20, and is fixed to a substantially semicircular bracket 13. As the bracket 13 is fixed to an inner peripheral surface of the plug 26 illustrated in FIGS. 4 to 6, the light guide rod 12 is supported by the plug 26.

In addition, as illustrated in FIG. 9, an elastic O-ring 40 is fitted to an outer peripheral surface of the light guide rod 12, and the light guide rod 12 is fitted into the lead-out hole 38 (see FIG. 5) via the O-ring 40. The O-ring 40 is an example of a third sealing member that is arranged in a gap between an outer peripheral surface configuring an outer wall surface of the light guide rod 12 and an inner peripheral surface configuring an inner wall surface of the lead-out hole 38 and is a component of the present invention. The O-ring 40 is also one of the plurality of sealing members that seal the inside of the exterior case 20, like the O-ring 36.

Referring back to FIG. 5, the side wall part 32D of the mount portion 32 comprises a lead-out hole 42 that leads the pin 18 (see FIG. 3) to the outside. The lead-out hole 42 is an example of a first lead-out hole, which is a component of the present invention.

As illustrated in FIG. 9, one end of the pin 18 is fixed to an inner case wall part 23, which is a front surface of the shield case 22, and the other end of the pin 18 is disposed to face the front. In addition, an elastic O-ring 44 is fitted to an outer peripheral surface of the pin 18, and the pin 18 is fitted into the lead-out hole 42 (see FIG. 5) via the O-ring 44. The O-ring 44 is an example of a first sealing member that is arranged in a gap between an outer peripheral surface configuring an outer wall surface of the pin 18 and an inner peripheral surface configuring an inner wall surface of the lead-out hole 42 and is a component of the present invention. The O-ring 44 is also one of the plurality of sealing members that seal the inside of the exterior case 20, like the O-rings 36 and 40.

In addition, by fitting the pin 18 into the lead-out hole 42 via the O-ring 44, the shield case 22 (see FIG. 1) is disposed inside the exterior case 20 by the pin 18. That is, the shield case 22 is disposed to be spaced apart from the inner surfaces of the plug 26 and the connector exterior case 28 by the pin 18.

Figure 10:
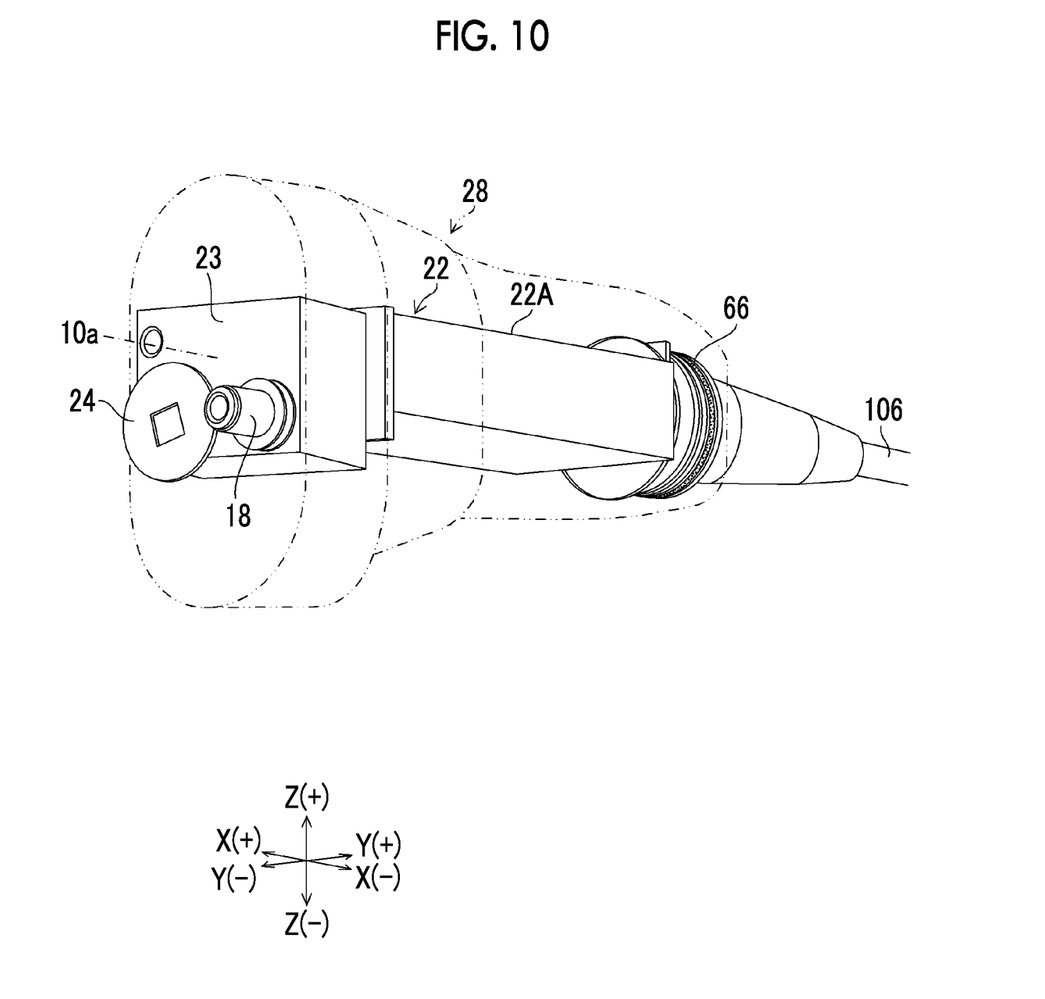
FIG. 10 is a perspective view illustrating a configuration of a shield case.

FIG. 10 is a perspective view illustrating a configuration of the shield case 22. As illustrated in FIG. 10, the shield case 22 is formed in a rectangular parallelepiped shape, and a long side 22A of the shield case 22 is accommodated in the connector exterior case 28 in a posture along the longitudinal axis 10a. Accordingly, a sufficient space is secured between the inner surface of the connector exterior case 28 and an outer surface of the shield case 22.

As illustrated in FIGS. 7 and 8, the connector exterior case 28 is formed in a substantially cylindrical shape with a bulging front end. The connector exterior case 28 comprises the elliptical ring portion 46 that has an opening 27 in the front end. The elliptical ring portion 46 is configured to have a shape in plan view that is a race track shape (oval shape), in which a pair of parallel linear portions 46A and 46A, which face each other in the right-and-left direction, and a pair of curved portions 46B and 46B, which face each other in the up-and-down direction, are connected to each other.

The connector exterior case 28 and the plug 26 (see FIG. 6) are connected to each other by fitting the elliptical ring portion 30 of the plug 26 into the elliptical ring portion 46 of the connector exterior case 28. In this connected state, the linear portions 30A and 30A of the elliptical ring portion 30 and the linear portions 46A and 46A of the elliptical ring portion 46 are disposed to face each other, and the curved portions 30B and 30B of the elliptical ring portion 30 and the curved portions 46B and 46B of the elliptical ring portion 46 are disposed to face each other. Then, as illustrated in FIG. 7, an inner peripheral surface of the elliptical ring portion 46 comprises an annular groove 48 along the inner peripheral surface, and the O-ring 36 (see FIG. 5) on a plug 26 side is fitted to the groove 48. That is, the connector exterior case 28 and the plug 26 are connected to each other by fitting the elliptical ring portion 30 of the plug 26 into the elliptical ring portion 46 of the connector exterior case 28 and fitting the O-ring 36 to the groove 48 (see FIG. 3).

On the other hand, as illustrated in FIG. 8, the linear portions 46A and 46A of the elliptical ring portion 46 comprises a pair of through-holes 50 and 52 (only the through-holes 50 and 52 in a left surface of the elliptical ring portion 46 are illustrated) penetrating an outer peripheral surface and the inner peripheral surface of the elliptical ring portion 46, which are coaxial in the up-and-down direction. In addition, as illustrated in FIG. 7, each of inner peripheral surfaces of the linear portions 46A and 46A comprises a semicircular groove 54, which connects the through-hole 50 and the through-hole 52 to each other, along the up-and-down direction. Further, as illustrated in FIGS. 4 and 5, outer peripheral surfaces of the linear portions 30A and 30A of the elliptical ring portion 30 comprise semicircular grooves 56 and 56 (only the grooves 56 in a left surface of the elliptical ring portion 30 are illustrated) along the up-and-down direction, and the grooves 56 are disposed to face the grooves 54 in a state where the connector exterior case 28 and the plug 26 are connected to each other. Accordingly, as in a cross sectional view of main parts illustrated in FIG. 11, a substantially cylindrical insertion passage 58 is formed along the up-and-down direction by a wall surface of the groove 54 and a wall surface of the groove 56.

Figure 11:
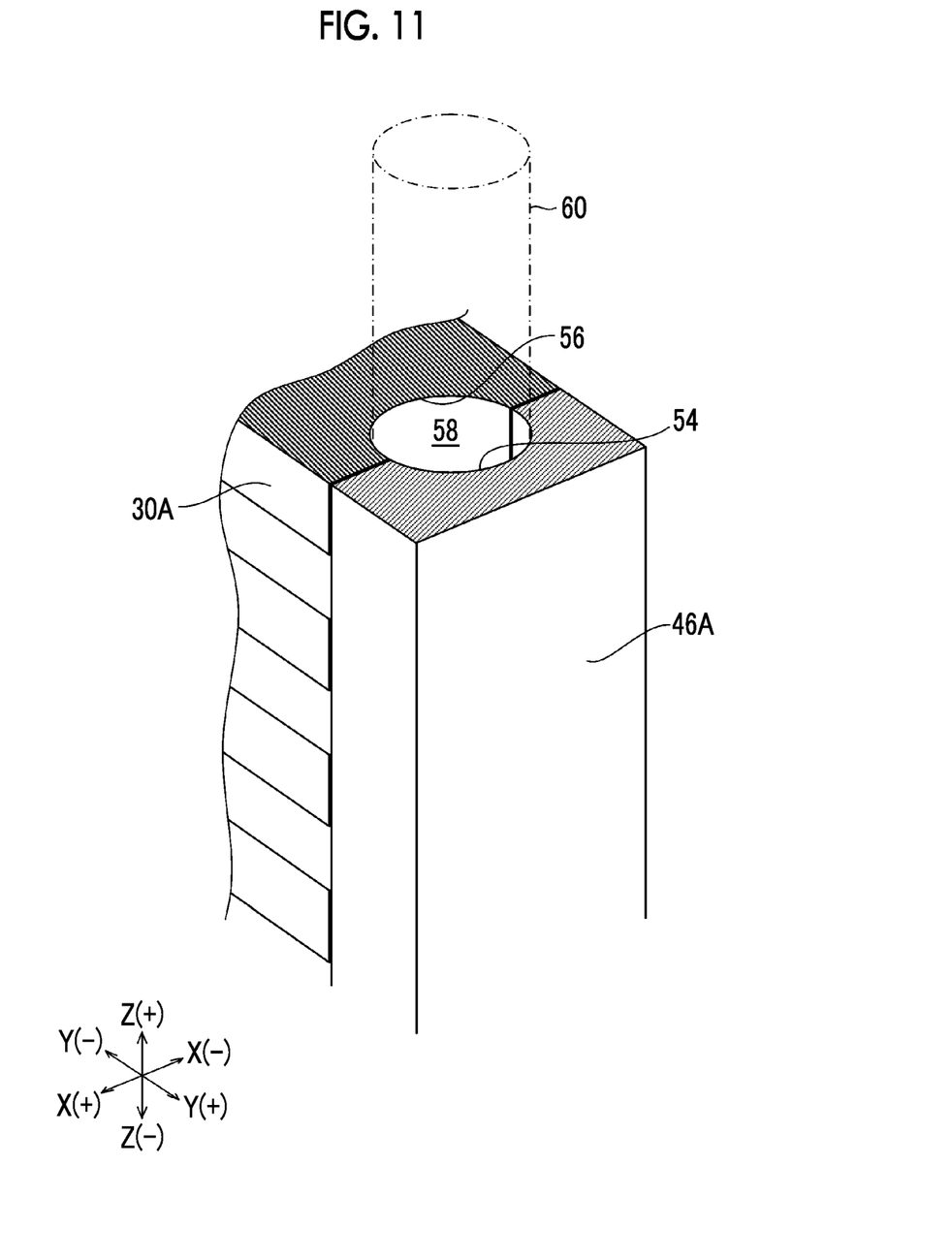
FIG. 11 is an enlarged cross sectional view of main parts, which illustrates an insertion passage into which a pin is inserted.

FIG. 8 illustrates a cylindrical pin 60 fitted from the through-hole 50 into the through-hole 52 via the insertion passage 58 (see FIG. 11). The pin 60 is fitted from the through-hole 50 into the through-hole 52 via the insertion passage 58 (see FIG. 11), an upper end part 60A of the pin 60 is fitted to an inner wall surface of the through-hole 50, a lower end part 60B of the pin 60 is fitted to an inner wall surface of the through-hole 52, and a portion of the pin 60 excluding the upper end part 60A and the lower end part 60B is fitted to the insertion passage 58. Accordingly, the plug 26 is prevented from coming off from the connector exterior case 28, and the linear portion 30A of the elliptical ring portion 30 is reinforced by the pin 60, causing a state where the deformation of the linear portion 30A is suppressed. In addition, the pin 60 is fastened to the elliptical ring portion 30 by a screw 62 (see FIG. 7) screwed from the lower end part 60B to the linear portion 30A of the elliptical ring portion 30. Accordingly, the pin 60 is prevented from falling off. Further, the upper end part 60A and the lower end part 60B of the pin 60 are composed of slopes so as not to protrude from the outer peripheral surface of the linear portion 46A. The pin 60 is preferably made of a metal having high stiffness.

As illustrated in FIG. 8, the connector exterior case 28 comprises, in a rear end thereof, an opening portion 64 to which the universal cable 106 (see FIG. 3) is connected. In addition, an elastic O-ring 66 (see FIG. 10) is fitted to an outer peripheral surface of the universal cable 106, and the universal cable 106 is fitted into the opening portion 64 via the O-ring 66. The O-ring 66 is an example of a second sealing member that is arranged in a gap between an outer peripheral surface configuring an outer wall surface of the universal cable 106 and an inner peripheral surface configuring an inner wall surface of the opening portion 64 and is a component of the present invention. The O-ring 66 is also one of the plurality of sealing members that seal the inside of the exterior case 20, like the O-rings 36, 40, and 44.

When assembling the endoscope 100 illustrated in FIG. 1, the insertion part 102, the grip portion 104, the switch disposed member 108, and the universal cable 106 are inserted into the outside from the opening 27 (see FIG. 7) of the connector exterior case 28 via the opening portion 64 (see FIG. 8), starting from the insertion part 102. For this reason, the opening portion 64 of the connector exterior case 28 is configured in a size that allows the insertion part 102, the grip portion 104, the switch disposed member 108, and the universal cable 106 to be inserted therein. By configuring the opening portion 64 in such a size, it becomes easy to assemble the endoscope 100. In addition, even when disassembling the endoscope 100, it becomes easy to disassemble the endoscope. It is more preferable that the opening portion 64 has a size that allows the insertion even in a state where the operation switch 110 is disposed on the switch disposed member 108. That is, the inner diameter of the opening portion 64 may be set to be larger than the diameter of a circumscribed circle of the switch disposed member 108 including the operation switch 110 when viewed from a longitudinal axis direction of the universal cable 106.

However, in the connector device 10 of the embodiment, as illustrated in FIGS. 9 and 10, inside the exterior case 20, the inner case wall part 23 of the shield case 22 is disposed to face and be spaced apart from the side wall part 32D (see FIG. 5) toward the rear, and the power reception unit 24 is disposed on the inner case wall part 23. That is, in the connector device 10 of the embodiment, since the inner case wall part 23 is disposed at a position spaced apart from the side wall part 32D toward the rear, which is a position unlikely to be affected by a heat cycle of steam sterilization and the power reception unit 24 is disposed on the inner case wall part 23, the following effects can be obtained.

For example, even in a case where the shape of the exterior case 20 (in particular, the plug 26) is deformed by the effect of the heat cycle of steam sterilization, a position shift of the power reception unit 24 can be suppressed since the power reception unit 24 is disposed on the inner case wall part 23 which is unlikely to be affected by the heat cycle. Accordingly, since a decrease in feeding efficiency attributable to the position shift of the power reception unit 24 can be suppressed, the endoscope 100 can be stably operated.

As described above, in the connector device 10 of the embodiment, the endoscope 100 can be stably operated since the exterior case 20 has the side wall part 32D facing the power feed unit 216, the shield case 22 has the inner case wall part 23 disposed to face and be spaced apart from the side wall part 32D, and the power reception unit 24 is disposed on the inner case wall part 23.

In addition, since the inner case wall part 23 is made of a metal, the amount of deformation caused by being affected by the heat cycle is extremely smaller than the resin exterior case 20. Accordingly, since the position shift of the power reception unit 24 can be effectively suppressed, the operation of the endoscope 100 is more stabilized.

In addition, since the core of the secondary coil configuring the power reception unit 24 is composed of a highly heat-resistant sintered ferrite core and the power reception unit 24 is adhered to the shield case 22 using a highly heat-resistant thermosetting epoxy sheet, the highly heat-resistant power reception unit 24 that can withstand sterilization by the autoclave can be provided.

In addition, by fixing the power reception unit 24 to a shield case 22 side, workability of arranging a lead wire from the power reception unit 24 to the shield case 22 side and workability of connecting the lead wire to a substrate of the shield case 22 improve, and disassembling work of the shield case 22 and the plug 26 also becomes easy.

In addition, in the connector device 10 of the embodiment, the shield case 22 is disposed to be spaced apart from the inner surface of the plug 26 and the inner surface of the connector exterior case 28 as being disposed in the exterior case 20 via the pin 18. With this configuration, the connector device 10 of the embodiment can obtain the following effects.

That is, in a case where the endoscope 100 comprising the connector device 10 is taken out from a high-pressure steam sterilizer, the temperature of the connector device 10 heated by the high-pressure steam sterilizer is gradually decreased by outside air. Herein, for example, in a case where a configuration in which the shield case 22 is in contact with the exterior case 20, in particular, the inner surface of the connector exterior case 28 is adopted, a temperature difference between the connector exterior case 28 and the shield case 22 is unlikely to occur in the process of decreasing the temperature after sterilization. Thus, moisture in the air inside the connector exterior case 28 adheres to an inner wall and the substrate of the shield case 22 and condensation occurs, causing a problem of adversely affecting the substrate. That is, condensation occurs also on an inner wall of the connector exterior case 28, but simultaneously with the condensation or without a time lag therebetween, condensation occurs on the inner wall and the substrate of the shield case 22.

On the contrary, in the connector device 10 of the embodiment, as the shield case 22 is held by the exterior case 20 via the pin 18, the outer surface of the shield case 22 is disposed to be spaced apart from the inner surface of the plug 26 and the inner surface of the connector exterior case 28. In addition, in the connector device 10 of the embodiment, as the connector exterior case 28 accommodates the shield case 22 in a posture in which the long side 22A of the shield case 22 is aligned with the longitudinal axis 10a, a sufficient space is secured between an inner surface of the exterior case 20 and the outer surface of the shield case 22. Therefore, condensation is unlikely to occur on the outer surface of the shield case 22 in the connector device 10 of the present embodiment. Accordingly, in the connector device 10 of the present embodiment, condensation on the substrate disposed inside the shield case 22 can be prevented.

In addition, in the connector device 10 of the embodiment, since the outer surface of the shield case 22 is disposed to be spaced apart from the inner surface of the plug 26 and the inner surface of the connector exterior case 28, internal stress caused by a temperature difference between the connector exterior case 28 and the shield case 22 can be reduced. Accordingly, heat cycle resistance attributable to steam sterilization improves.

In addition, in the connector device 10 of the present embodiment, since a sufficient space is secured between the inner surface of the exterior case 20 and the outer surface of the shield case 22, time constant (relaxation time) representing time required for the heat of the high-pressure steam sterilizer to be transmitted to an electrical component such as a substrate increases. Accordingly, thermal stress on the electrical component can be reduced.

In addition, in the connector device 10 of the embodiment, the plug 26 and the connector exterior case 28, which configure the exterior case 20, are preferably made of, for example, a polyphenylsulfone resin, the light guide rod 12 and the pins 18 and 60 are preferably made of, for example, stainless steel, and the O-rings 36, 40, 44, and 66 are preferably made of, for example, highly heat-resistant fluororubber.

In addition, although an aspect in which the power reception unit 24 is disposed on the inner case wall part 23 of the shield case 22 in the connector device 10 of the embodiment is given as an example, the inner case wall part on which the power reception unit 24 is disposed is not limited to the shield case 22, that is, may be an inner case accommodated inside the exterior case 20, or may be, for example, an inner case that covers the shield case 22. In this case, it is preferable that the inner case is made of a metal.

In addition, although the plug 26 and the connector exterior case 28, which are examples of the exterior case, are made of a resin and the shield case 22, which is an example of the inner case, is made of a metal as a preferable aspect in the embodiment, without being limited thereto, the exterior case and the inner case may be made of other materials.

In addition, the shapes of the elliptical ring portion 30 and the elliptical ring portion 46, which are connecting portions between the plug 26 and the connector exterior case 28, are a race track shape as a preferable aspect in the embodiment, but without being limited thereto, may be an oval shape (a shape that is not symmetrical with a line in a minor axis direction passing through an intersection between a major axis direction and the minor axis direction as a center line) such as a circle, an ellipse, and an egg shape in plan view insofar as the shape is a shape that can connect the plug 26 and the connector exterior case 28 to each other.

In addition, although the core of the secondary coil configuring the power reception unit 24 is configured by a sintered ferrite core as a preferable aspect in the embodiment, the core may be made of other materials. In addition, the power reception unit 24 is adhered to the shield case 22 by a thermosetting adhesive material, but may be adhered to the shield case 22 by other adhesive materials.

Although the present invention has been described hereinbefore, the present invention is not limited to the examples, and it is evident that various improvements and modifications may be made without departing from the gist of the present invention.

EXPLANATION OF REFERENCES

1: endoscope system
10: connector device
10a: longitudinal axis
12: light guide rod
13: bracket
14: image signal transmission unit
16: fiber cable
16A: light emission end
18: pin
20: exterior case
22: shield case
22A: long side
23: inner case wall part
24: power reception unit
26: plug
28: connector exterior case
30: elliptical ring portion
30A: linear portion
30B: curved portion
32: mount portion
32A: linear portion
32B: curved portion
32C: linear portion
32D: side wall part
34: cylindrical portion
36: O-ring
38: lead-out hole
40: O-ring
42: lead-out hole
44: O-ring
46: elliptical ring portion
46A: linear portion
46B: curved portion
48: groove
50: through-hole
52: through-hole
54: groove
56: groove
58: insertion passage
60: pin
60A: upper end part
60B: lower end part
62: screw
64: opening portion
66: O-ring
100: endoscope
102: insertion part
102A: distal end surface
104: grip portion
106: universal cable
108: switch disposed member
110: operation switch
114: observation part
116: observation window
118: light guide
118A: light emission end
118B: light incident end
120: image pick-up lens group
122: prism
124: solid-state imaging element
126: signal line
200: processor device for an endoscope
202: light source unit
204: image signal reception unit
206: image processing unit
208: monitor
210: processor side connector
212: connection hole
214: connection hole
216: power feed unit

What is claimed is:

1. A connector device for an endoscope that is attachably and detachably connected to a processor device, the connector device comprising:
   a hollow exterior case;
   an inner case that is accommodated inside the exterior case;
   a holding body for disposing the inner case inside the exterior case; and
   a power reception unit to which power is supplied from a power feed unit of the processor device in a contactless manner,
   wherein the exterior case has a side wall part that faces the power feed unit of the processor device,
   the inner case has an inner case wall part that is disposed to face and be spaced apart from the side wall part,
   the power reception unit is disposed on the inner case wall part,
   the holding body is a shaft-shaped member, one end of the shaft-shaped member is fixed to the inner case wall part,
   a first lead-out hole that leads the other end of the shaft-shaped member to an outside of the exterior case is provided in the side wall part,
   the shaft-shaped member is inserted into the first lead-out hole, and
   a first sealing member is arranged between an inner wall surface of the first lead-out hole and an outer wall surface of the shaft-shaped member.

2. The connector device for the endoscope according to claim 1,
   wherein the power reception unit has a flat plate-shaped core and a coil that is spirally wound around the core, and
   the core is composed of a sintered ferrite core.

3. The connector device for the endoscope according to claim 1,
   wherein the power reception unit is adhered to the inner case wall part by a thermosetting adhesive material.

4. The connector device for the endoscope according to claim 1,
   wherein the processor device has a positioning hole in a surface facing the side wall part, and
   the other end of the shaft-shaped member is inserted into the positioning hole, and the power reception unit is in a state of being positioned at a position facing the power feed unit.

5. The connector device for the endoscope according to claim 1,
   wherein the first sealing member is an O-ring fitted to the outer wall surface of the shaft-shaped member.

6. The connector device for the endoscope according to claim 1,
   wherein the exterior case is made of a resin, and
   the inner case is made of a metal.

7. The connector device for the endoscope according to claim 1,
   wherein the inner case is a shield case for shielding an electronic component.

8. The connector device for the endoscope according to claim 1,
   wherein the exterior case has a cylindrical body,
   the inner case is formed in a rectangular parallelepiped shape, and
   the inner case is accommodated in the exterior case in a posture in which a long side of the inner case is aligned with an axis of the cylindrical body.

9. The connector device for the endoscope according to claim 1,
   the exterior case has an opening portion to which a universal cable extending from the endoscope is connected, and
   a second sealing member is arranged between an inner wall surface of the opening portion and an outer wall surface of the universal cable.

10. The connector device for the endoscope according to claim 9,
    wherein the second sealing member is an O-ring fitted to the outer wall surface of the universal cable.

11. The connector device for the endoscope according to claim 9,
    wherein the opening portion of the exterior case is formed in a size that allows the endoscope, the universal cable, and a switch disposed member provided at the universal cable to be inserted therein.

12. The connector device for the endoscope according to claim 1, further comprising:
    a light guide rod, one end of the light guide rod being disposed inside the exterior case,
    wherein a second lead-out hole that leads the other end of the light guide rod to the outside of the exterior case is provided in the side wall part,
    the light guide rod is inserted into the second lead-out hole, and
    a third sealing member is arranged between an inner wall surface of the second lead-out hole and an outer wall surface of the light guide rod.

13. The connector device for the endoscope according to claim 12,
    wherein the third sealing member is an O-ring fitted to the outer wall surface of the light guide rod.

* * * * *